United States Patent
Wang et al.

(10) Patent No.: US 6,710,873 B2
(45) Date of Patent: Mar. 23, 2004

(54) TEMPERATURE-INDEPENDENT MEASUREMENTS OF GAS CONCENTRATION

(75) Inventors: Jian Wang, Hangzhou (CN); Ronald K. Hanson, Cupertino, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 113 days.

(21) Appl. No.: 09/991,362

(22) Filed: Nov. 16, 2001

(65) Prior Publication Data

US 2002/0135762 A1 Sep. 26, 2002

Related U.S. Application Data (60) Provisional application No. 60/249,522, filed on Nov. 17, 2000.

(51) Int. Cl.$^7$ .............................. G01J 3/28; G01J 3/40; G01J 3/50; G01J 5/02
(52) U.S. Cl. ..................... 356/326; 356/302; 250/226; 250/339.07; 250/343; 250/345
(58) Field of Search ................. 356/319, 302, 356/326, 945; 250/226, 339.07, 343, 345

(56) References Cited

U.S. PATENT DOCUMENTS 3,723,731 A * 3/1973 Blau, Jr.
3,790,798 A * 2/1974 Sternberg et al.
3,811,776 A * 5/1974 Blau, Jr.

(List continued on next page.)

OTHER PUBLICATIONS

Bishop G.A., et al., "IR Long–Path Photometry: A Remote Sensing Tool for Automobile Emissions," Anal. Chem. A., 1989, vol. 61, pp. 671–677.

(List continued on next page.)

*Primary Examiner*—Frank G. Font
*Assistant Examiner*—Khaled Brown
(74) *Attorney, Agent, or Firm*—Lumen Intellectual Property Services, Inc.

(57) ABSTRACT

A method and apparatus for temperature-independent determination of a concentration of a probe gas in a sample over a selected temperature range between a low temperature $T_L$ corresponding to a lowest temperature expected or found in the sample and a high temperature $T_H$ corresponding to a highest temperature expected or found in the sample. In accordance with the method, a probe temperature function of the probe gas is determined over the temperature range using a first spectroscopic technique. Then, a second spectroscopic technique is selected, a reference gas is identified and a reference temperature function of the reference gas is determined using the second spectroscopic technique over the temperature range. In particular, the reference gas is identified such that a ratio of the probe temperature function and the reference temperature function is substantially constant over the temperature range. A probe reaction of the probe gas and a reference reaction of the reference gas is then measured by the first and second spectroscopic techniques and the concentration of the probe gas is derived from the probe reaction and reference reaction. The method of the invention can be take advantage of spectroscopic techniques such as absorption spectroscopy employing a test beam of light at several wavelengths with at least one wavelength for either probe transition or reference transition. The method and apparatus can be used in monitoring various gas samples and are especially well-suited for determining probe gas concentrations in samples which exhibit non-uniformities in temperature, pressure and gas composition, e.g., as encountered in vehicle exhaust samples.

28 Claims, 3 Drawing Sheets

U.S. PATENT DOCUMENTS

3,979,589 A * 9/1976 Sternberg et al.
4,394,575 A * 7/1983 Nelson
4,520,265 A * 5/1985 Griggs et al.
5,153,436 A * 10/1992 Apperson et al.
5,498,872 A    3/1996 Stedman et al. ......... 250/338.5
6,157,455 A * 12/2000 Pinvidic et al.
6,420,695 B1 * 7/2002 Grasdepot et al.

OTHER PUBLICATIONS

Cadle S.H., et al., "Remote Sensing of Vehicle Exhaust Emissions," Environ. Sci. Technol. A, 1994, vol. 28, pp. 258–264.

Stephens R.D., et al., "Remote Sensing Measurements of Carbon Monoxide Emissions from On–Road Vehicles," J. Air Waste Management Assoc., 1991, vol. 41, pp. 39–46.

* cited by examiner

TEMPERATURE-INDEPENDENT MEASUREMENTS OF GAS CONCENTRATION

RELATED APPLICATIONS

This application claims priority from U.S. Provisional Patent Application No. 60/249,522, filed on Nov. 17, 2000 and which is herein incorporated by reference.

STATEMENT REGARDING FEDERALLY SPONSORED RESEARCH OR DEVELOPMENT

This invention was supported in part by grant number F49620-98-1-0010 awarded by the Air Force Office of Scientific Research (AFOSR). The U.S. Government has certain rights in the invention.

FIELD OF THE INVENTION

This invention relates generally to using spectroscopic techniques for gas concentration measurements, and in particular to using a ratio of gas concentrations to obtain temperature-independent measurements.

BACKGROUND AND PRIOR ART

Gas concentrations are measured in laboratory experiments, industrial plant operations as well as monitoring and sensing in public or private areas. In some of these cases the measurements are performed to determine what chemical reactions are taking place, in others they represent direct results, e.g., concentrations of pollutants in the atmosphere such as exhausts from stack and vehicles (smog check and on-road remote sensing).

Gas concentration sensors based on spectroscopic techniques and absorption spectroscopy in particular have been widely used for many industrial applications as well as vehicle exhaust monitoring. For general information on the use of absorption spectroscopy, including IR and UV absorption for monitoring vehicle emissions the reader is referred to: Bishop G. A., et al., *IR long-path photometry: a remote sensing tool for automobile emissions*, Anal. Chem. A, 1989, Vol. 61, pp. 671–77; Cadle S. H., et al., *Remote sensing of vehicle exhaust emissions*, Environ. Sci. Technol. A, 1994, Vol. 28, pp. 258–64; Stephens R. D., et al., Remote sensing measurements of carbon monoxide emissions from on-road vehicles, J. Air Waste Management Assoc., 1991, Vol. 41, pp. 39–46. In addition, U.S. Pat. No. 5,498,872 to Stedman et al. teaches an apparatus for remote analysis of vehicle emissions in vehicle exhaust including, for example, concentrations of CO, $CO_2$, HC, NO and $H_2O$ by using wide-band radiation.

The above-mentioned references take advantage of known absorption techniques which measure gas concentrations by monitoring the attenuation of optical radiation passing through the sample containing the probe gas. Attenuation of the optical radiation is due to optical radiation getting absorbed at wavelengths corresponding to certain transitions in the molecules of the probe gas. In other words, when the incident radiation contains photons at wavelengths corresponding to absorbing transitions, also referred to as spectroscopic transitions of the probe gas molecules, then some of these photons will be absorbed by the probe gas molecules. The attenuation is generally proportional to the amount of the probe gas molecules encountered by the radiation along its path. In addition, the amount of attenuation suffered by optical radiation passing through a sample of the probe gas is dependent on the gas temperature and the gas mixture composition of the sample. That is because these parameters affect the linestrength and linewidth of the selected transition or transitions. In order to correct for these effects prior art methods require temperature and gas composition information.

Unfortunately, in many situations the temperature and gas composition data required by prior art methods to correct for linestrength and linewidth is unknown. In other cases, gas composition and/or temperature measurements are not feasible or difficult. In the example of on-road remote sensing of vehicle exhausts, the temperature and composition distributions along the optical beam path are non-uniform and unknown. Similar problems are encountered in monitoring emissions from stacks, especially into turbulent and hence non-uniform atmosphere.

These limitations lead to errors of traditional absorption spectroscopy techniques in determining concentrations of probe gases. These errors are especially large in samples exhibiting large non-uniformities and/or significant fluctuations of temperature and composition profiles along the probe beam path. It would be an advance in the art to provide a technique for measuring a concentration of a probe gas in a sample without the need to determine the temperature and gas composition along the path of the probe beam of the spectrometer.

OBJECTS AND ADVANTAGES

In view of the above, it is an object of the invention to provide a spectroscopic method for accurately determining the concentration of a probe gas in a sample without the necessity to determine the temperature and gas composition of the sample. Specifically, the method of the invention does not require knowledge of the temperature and gas composition along the path of the probe beam for line-of-sight absorption spectroscopy techniques. For point measurement spectroscopy such as laser induced fluorescence, the method does not require knowledge of the temperature and composition at that point.

It is another object of the invention to ensure that the method of the invention can be practiced in monitoring emissions in environments which are uncontrolled and in environments where gas temperature and composition are unknown. Specifically, it is an object of the invention to adapt the method for monitoring emissions from stacks and exhaust emissions from vehicles such as cars and airplanes.

Yet another object of the invention is to provide an apparatus for practicing the method of the invention.

These as well as other objects and advantages will become apparent upon review of the following detailed description.

SUMMARY

The objects and advantages of the invention are achieved by a method for temperature-independent determination of a concentration of a probe gas in a sample. First, a temperature range is selected. Preferably, the temperature range extends from a low temperature $T_L$ corresponding to a lowest temperature expected or found in the sample and a high temperature $T_H$ corresponding to a highest temperature expected or found in the sample. Next, a first spectroscopic technique is selected and a probe temperature function of the probe gas is determined over the temperature range using that first spectroscopic technique. Then, a second spectroscopic technique is selected and a reference gas is identified. A reference temperature function of the reference gas is determined using the second spectroscopic technique over the temperature range. It should be noted that the first and second spectroscopic techniques can be the same. The reference gas is identified such that a ratio of the probe temperature function and the reference temperature function is substantially constant over the temperature range. For example, the ratio of the temperature functions can be substantially equal to one over the temperature range. A probe reaction of the probe gas and a reference reaction of the reference gas is then measured by the first and second spectroscopic techniques and the concentration of the probe gas is derived from the probe reaction and reference reaction.

In one embodiment either one or both of the spectroscopic techniques are absorption spectroscopy employing a test beam. The test beam consists of light at several wavelengths with at least one wavelength for either probe transition or reference transition. The test beam passing through the sample causes the probe gas and the reference gas to absorb wavelength components of the light of the test beam corresponding to the probe and reference transitions. In other words, probe reaction is a probe absorption of a wavelength component corresponding to a probe absorption transition used for detecting the probe gas. Similarly, reference reaction is a reference absorption of a wavelength component corresponding to a reference absorption transition used for detection of the reference gas.

At the detection side, the light of the test beam is separated by wavelength using appropriate optical components. For example, different wavelength components can be split and directed to separate photodetectors. The attenuations corresponding to the probe and reference transitions can then be obtained from signals detected at the different photodetectors.

The absorptive transitions of the probe gas and reference gas at which absorption occurs can be selected from any suitable transitions. For molecular gas species the transitions can be selected from rotational, rovibrational and rovibronic transitions. For atomic gas species the transitions are electronic transitions. Selection of these transitions can be based on a vector difference between the ratio of the probe and reference temperature functions and a constant value. Preferably, the transitions for which the smallest vector difference is obtained are selected to thus minimize the temperature effect.

In the same or another embodiment the spectroscopic techniques use broadband light sources spanning broadband spectra. In this case the overall absorption of light by the probe gas and the reference gas can be measured. The reference temperature function in this embodiment can be obtained from a linear combination of a first reference temperature function in a first portion of the broadband spectrum and a second reference temperature function in a second portion of the broadband spectrum. For example, the first reference temperature function is associated with measurements with a first broadband source and the second reference temperature is associated with the second broadband source. Such linear combination can be used if the reference temperature function does not yield a sufficiently constant ratio of probe and reference temperature functions. Similarly, the probe temperature function can also be obtained from a linear combination of a first probe temperature function associated with the first broadband source and a second probe temperature function associated with the second broadband source.

In another embodiment the spectroscopic techniques employ narrowband sources having narrow spectral widths. In particular, the spectral widths are preferably narrower then the corresponding transition linewidths in the probe and reference gases. The probe reaction and reference reaction can be associated with corresponding transitions in the probe and reference gases. If the reference temperature function fails to yield a sufficiently constant ratio of probe and reference temperature functions a linear combination of functions can be employed. In particular, the reference reaction can be associated with a first transition and a second transition. The reference temperature function is now obtained from a linear combination of a first reference temperature function of the first transition and a second temperature function of the second transition.

When using a narrowband source, its spectral width is preferably narrower, even much narrower than the linewidths of the reference transitions. In the case of using two transitions in the probe gas in a linear combination, the spectral width should be narrower than the linewidth of each of these. The probe reaction can be an attenuation resulting from a probe transition and the spectral width of the narrowband source should be narrower than the linewidth of that probe transition.

In deriving the concentration of the probe gas it is convenient to derive a measured concentration ratio of the probe gas to said reference gas. This measured concentration ratio can be obtained with the aid of known techniques from the probe and reference reactions, e.g., amount of absorption by the transitions in the probe and reference gases.

The probe and reference temperature functions can be indexed to a reference temperature $T_{ref}$. Although $T_{ref}$ can be selected outside the temperature range, it is convenient that $T_{ref}$ be chosen within the temperature range such that $T_L \leq T_{ref} \leq T_H$.

The selection of reference gas in the sample can be based, in addition to the conditions discussed above, on other characteristics of the gas. It is convenient to choose as reference gas one that is stable and has a functional relationship with the probe gas. The functional relationship can be a well-established relation between the gas concentrations under some known conditions. This functional relationship can then be used in deriving the concentration of the probe gas. For example, in one embodiment, the probe gas is CO and the reference gas is $CO_2$. A sample containing these two can be a vehicle exhaust sample.

The method of the invention is particularly well-suited for determining probe gas concentrations in samples which exhibit non-uniformities. Among these non-uniformities are temperature, pressure and gas composition non-uniformities, e.g., as encountered in vehicle exhaust samples.

An apparatus for temperature-independent determination of probe gas concentration has a spectrometer for employing the selected spectroscopic technique including techniques with broadband and narrowband light sources. A laser is preferably used as the narrowband source. The apparatus also has a processing unit for determining the probe and reference temperature functions such that their ratio is substantially constant over the temperature range. A computing unit is provided for deriving the probe gas concentration from the probe and reference reactions.

The apparatus additionally includes a unit for calculating the ratio of temperature functions. Furthermore, the apparatus has optics for directing the probe beam from light sources to the detectors employed by the spectrometer.

The details of the invention are explained in the below detailed description with reference to the attached drawing figures.

DETAILED DESCRIPTION

Figure 1:
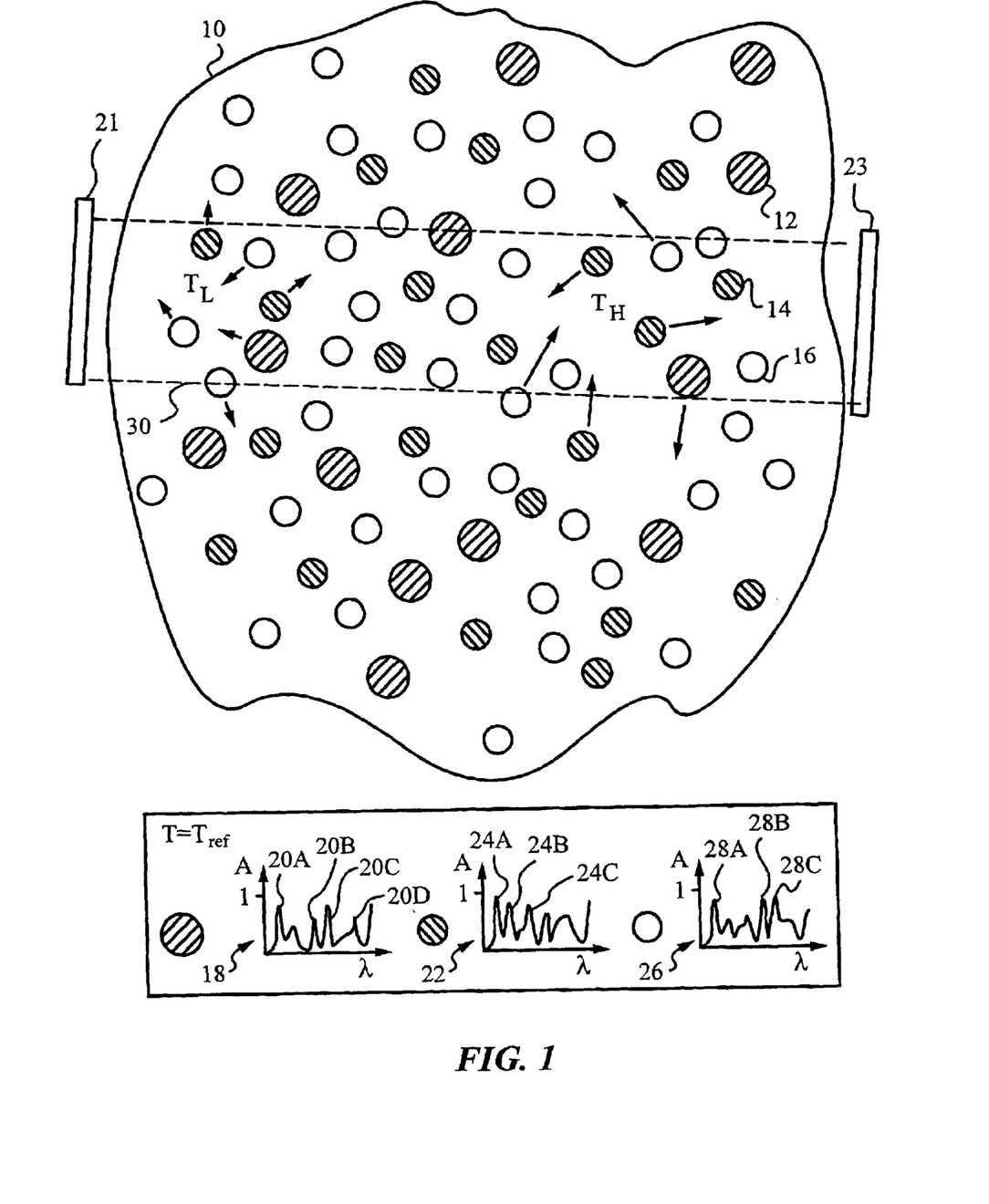
FIG. 1 is a schematic diagram illustrating the theoretical foundations of the ratio-based concentration measurement method of the invention.

The invention will be best understood by initially referring to the schematic diagram of FIG. 1 illustrating a sample 10 of three gases 12, 14, 16. Sample 10 may contain additional gases which are not shown for reasons of clarity. Sample 10 can be located in a closed container or it can be an open sample, e.g., it can be a volume of arbitrary shape and not confined by any container. For example, gases 12, 14, 16 can be unconstrained gases found in the ambient atmosphere.

It is despaired to determine the concentration of gas 12 in sample 10. In other words, gas 12 is selected as a probe gas. It is well known that at a specific or constant temperature probe gas 12 has a certain spectrum 18 for electromagnetic radiation, specifically the optical portion of the radiation spectrum. Spectrum 18 indicates percent absorption A along the y-axis and from this spectrum it can be seen that probe gas has several absorption peaks. In the present case a reference temperature $T_{ref}$ is the constant temperature at which spectrum 18 is observed.

It should be noted that absorption spectrum 18 does not represent the absorption spectrum of any particular gas and serves illustrative purposes only. Absorption spectrum 18 has a number of absorption peaks or probe absorption transitions of which absorption transitions 20A, 20B, 20C and 20D are identified. Transitions 20A, 20B, 20C and 20D can be any transitions of the molecules of probe gas 12. For example, the transitions can be rotational transitions, rovibrational transitions and rovibronic transitions. In the event probe gas 12 is monoatomic all transitions are atomic transitions.

Similarly, gases 14, 16 also have certain absorption spectra 22, 26 at a specific temperature. Absorption peaks or absorption transitions 24A, 24B and 24C are identified in gas 14 and absorption transitions 28A, 28B and 28C are identified in gas 16. All three spectra 18, 22, 26 are shown at the same constant reference temperature $T_{ref}$.

Sample 10 is non-uniform in the sense that gases 12, 14, 16 in sample 10 are not distributed uniformly and the temperature in sample 10 varies from one region to another in a non-uniform manner. In practice these non-uniformities are frequently unknown, e.g., as is the case when sample 10 is a turbulent mixture of gases 12, 14, 16. It is important however, that the ratio of concentrations of any two gases in sample 10 remain constant in every region of sample 10, although the temperature and gas composition differ from region to region. Samples which satisfy this condition include, among other, exhaust from stacks or vehicles, e.g., car tailpipes.

In this example, the temperature varies between a known or estimated low temperature $T_L$ in a left region and a known or also estimated high temperature $T_H$ in a right region. The arrows indicate the velocities of the gas molecules in the low temperature $T_L$ and high temperature $T_H$ regions. Hence, depending on where probe gas 12 is in sample 10 it may be at a temperature as high as $T_H$ and as low as $T_L$, i.e., probe gas 12 can be found in a temperature range $(T_H-T_L)$ within sample. The same applies to gases 14, 16. As a result, absorption spectra 18, 22, 26 of gases 12, 14, 16 will vary due to linestrength and linewidth variations in the absorption transitions.

To perform a spectroscopic measurement a spectroscopic technique is selected. In the present embodiment the selected spectroscopic technique is absorption spectroscopy which uses light beam generator 21, which comprises narrowband light sources, e.g., single-mode lasers and appropriate wavelength division multiplexing components for generating a test beam 30. Corresponding receiver 23 that comprises appropriate wavelength division de-multiplexing components and detectors is provided to receive different wavelength components of test beam 30 after its passage through sample 10. The spectral width of each light source of generator 21 is much narrower than the linewidth of corresponding spectroscopic transitions, as further explained below.

To perform the spectroscopic measurement a probe reaction to the wavelength component in beam 30 corresponding to the probe spectroscopic transition is identified. In the case of narrowband absorption spectroscopy employed in this embodiment the probe reaction is an absorption of the wavelength component in test beam 30 corresponding to the probe spectroscopic transition. Specifically, transition 20B is selected and test beam 30 is generated to contain component wavelength $\lambda_i$ corresponding to transition 20B. Actually, it is preferable that the linewidth of transition 20B be larger or even significantly larger than the spectral width of wavelength component $\lambda_i$ in test beam 30.

The cross section of the beam path of probe beam 30 through sample 10 is indicated in dashed lines. Since the temperature of gases 12, 14, 16 along the beam path is non-uniform and unknown, a constant reference temperature $T_{ref}$ is assumed. Therefore, the measured probe concentration of probe gas 12, $[gas\ 12]_{meas}$, is a function of the true gas temperature T and is related to the true concentration of probe gas 12, $[gas\ 12]_{true}$, by:

$$[gas\ 12]_{meas}=[gas\ 12]_{true} \cdot F_{12}(T). \qquad (1A)$$

The function $F_{12}(T)$ is a probe temperature function which depends on the probe reaction, in this case absorption at absorption transition 20B. Probe temperature function $F_{12}(T)$ also depends on the selected spectroscopic measurement technique. The present embodiment uses a direct-absorption technique with narrowband source 21 with a spectral width much narrower than the probe absorption transition linewidth (e.g., the source is a single-longitudinal-mode laser) and integrates absorbance over the entire lineshape to eliminate the effect of linewidth. Therefore, the corresponding probe temperature function is:

$$F_{12}(T) = \frac{S_i(T)}{S_i(T_{ref})}. \qquad (2)$$

Here, $S_i$ is the linestrength of the i-th probe absorption transition, in this case transition 20B used in the measurement. Alternatively, when the peak absorbance at the center of probe absorption transition is used to determine gas concentration, then probe temperature function $F_{12}(T)$ becomes:

$$F_{12}(T) = \frac{S_i(T)\Delta v_i(T_{ref})}{S_i(T_{ref})\Delta v_i(T)}. \quad (3)$$

Equation (3) assumes a Lorentzian lineshape of the absorption transmission and $\Delta v_i$ is the absorption transition linewidth of the i-th transition, in this case both refer to transition 20B. In the case of wavelength modulation spectroscopy (WMS) technique the same probe temperature function $F_{12}(T)$ is obtained since the effect of the modulation index is negligible. In fact, given any particular spectroscopic technique, a person skilled in the art will recognize how the probe temperature function is to be adjusted by calculating $S(T)$ and $v(T)$ in any given situation. For additional information on this topic the reader is referred to J. Wang, et al., In Situ Measurements of CO Using Diode Laser Absorption Near 2.3 Microns, Applied Optics, Vol. 39, Oct. 20, 2000, pp. 5579–89.

Measured concentrations of gases 14, 16 are also governed by analogous relationships as probe gas 12. In the present absorption spectroscopic technique the reactions of these gases translate into absorptions and, once again, it is preferable that the corresponding wavelength components in beam 30 be narrower than the transitions in gases 14, 16, or at least the transitions in the gas selected as the reference gas. Now, when beam 30 contains the wavelength $\lambda_j$ corresponding to the absorption transition selected in gas 14, e.g., transition 24B, then the measured concentration of gas 14, [gas 14]$_{meas}$, is a function of the true gas temperature T and is related to the true concentration of gas 14, [gas 14]$_{true}$, by:

$$[\text{gas 14}]_{meas} = [\text{gas 14}]_{true} \cdot F_{14}(T). \quad (1B)$$

Similarly, in the case of gas 16 and using, e.g., absorption transition 28B:

$$[\text{gas 16}]_{meas} = [\text{gas 16}]_{true} \cdot F_{16}(T). \quad (1C)$$

In accordance with the method of the invention, one of gases 14, 16 in sample 10 is selected as the reference gas to probe gas 12. The selection of the reference gas is made such that a ratio of the probe temperature function to the reference temperature function is substantially constant. The substantial constancy of the ratio of the temperature functions has to extend over the temperature range confirmed or expected in sample 10. In this case the temperature range is $T_H$–$T_L$.

Identification of the reference gas and reference reaction, in the present embodiment reference transition, is most conveniently performed based on a comparison of temperature functions of available absorption transitions in probe gas 12 (probe absorption transitions) and in the candidate reference gases 14, 16. The final selection is made based on the degree of constancy of the ratio of the temperature functions over the temperature range. In addition, it is preferred that the gas selected as the reference gas be a stable gas and have a functional relationship with the probe gas, e.g, that a known relationship exist between their concentrations.

It is particularly convenient to set up a vector difference between the ratio of probe and reference temperature functions and a constant value to determine which pair of transitions minimizes this vector difference. The vector difference can be conveniently quantified by its vector norm such as infinity norm or 2 norm. A computer program such as MATLAB can be used to implement this vector difference computation.

In accordance with the invention, a ratio of measured probe concentration [gas 12]$_{meas}$ and measured reference concentration [gas 14]$_{meas}$ is set up as follows:

$$\left(\frac{[\text{gas 12}]}{[\text{gas 14}]}\right)_{meas} = \left(\frac{[\text{gas 12}]}{[\text{gas 14}]}\right)_{true} \cdot \left(\frac{F_{12}(T)}{F_{14}(T)}\right). \quad (4)$$

The second term on the right of equation 4 is the ratio of probe temperature function to reference temperature function. In the present embodiment gas 14 is selected as the reference gas in accordance with the above guidelines and as explained in reference to FIGS. 2 & 3.

Figure 2:
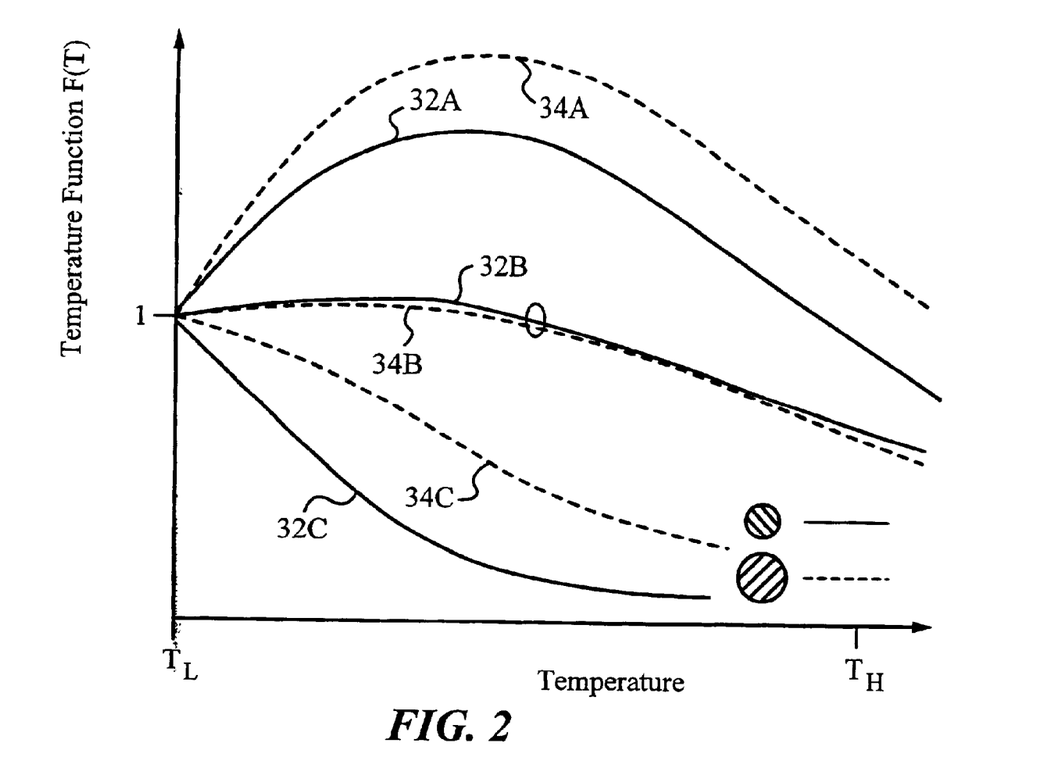
FIG. 2 is a graph illustrating probe and reference temperature functions.

FIG. 2 shows three probe temperature functions 32A, 32B and 32C associated with probe absorption transitions 20A, 20B, 20C respectively. FIG. 2 also shows three temperature functions 34A, 34B and 34C associated with absorption transitions 24A, 24B, 24C of gas 14 respectively. As can be seen, probe temperature function 32B associated with probe absorption transition 20B and reference temperature function 34B associated with reference absorption transition 24B differ from each other only minimally over the temperature range. In other words, $F_{12}(T) \approx F_{14}(T)$ over temperature range $T_H$–$T_L$ and hence the ratio of $F_{12}(T)/F_{14}(T)$ is substantially constant over that temperature range.

Figure 3:
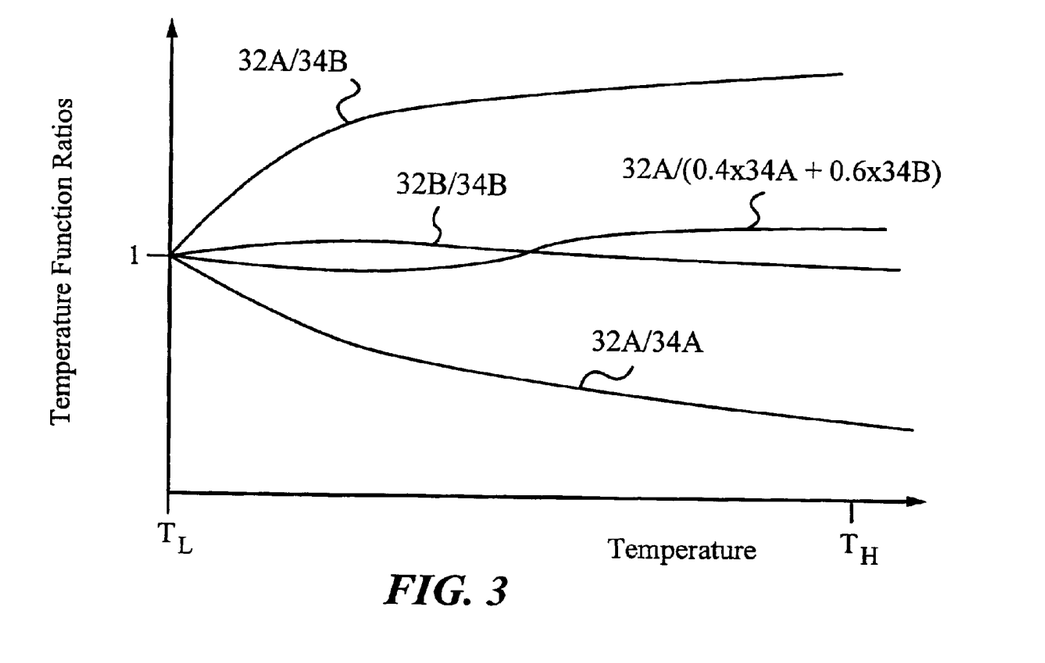
FIG. 3 is a graph illustrating ratios of reference and probe temperature functions.

FIG. 3 shows the ratios of temperature functions for the probe and reference transitions. Clearly, the ratio of temperature functions $F_{12}(T)/F_{14}(T)$ for probe transition 20B and reference transition 24B is substantially constant. Moreover, this ratio is substantially equal to one over the temperature range. Although, this is not required, it is convenient when the ratio is equal to one. In fact, if the reference temperature $T_{ref}$ is not selected in the temperature range from $T_L$ to $T_H$ the constant is most likely not going to be substantially equal to one.

Now the reason for selecting $F_{12}(T) \approx F_{14}(T)$ over temperature range $T_H$–$T_L$ becomes clear. Since the ratio of $F_{12}(T)/F_{14}(T)$ is approximately constant at any particular temperature T within temperature range $T_H$–$T_L$ the ratio is replaced by the constant. Now, the true concentration of probe gas 12 is obtained from the simplified ratio:

$$\left(\frac{[\text{gas 12}]}{[\text{gas 14}]}\right)_{true} = \text{constant} \cdot \left(\frac{[\text{gas 12}]}{[\text{gas 14}]}\right)_{meas} \quad (5)$$

In some cases this condition can not be ensured with by using a ratio based on the probe transition and a single reference transition. A linear combination of two or more reference temperature functions for corresponding two or more reference transitions can be used in this situations. From FIG. 3 it is clear that a ratio of probe temperature function 32A associated with probe transition 20A to a linear combination of reference temperature functions 34A and 34B is substantially constant over the temperature range. Reference temperature functions 34A, 34B are associated with transitions 24A, 24B in reference gas 14. The ratio uses a linear combination of reference temperature function 34A and of reference temperature function 34B as follows:

$$\frac{F_{12}(T)}{aF_{14(24A)}(T) + bF_{14(24B)}(T)} = \text{constant.} \quad (6)$$

In the particular case graphed in FIG. 3, the linear combination is constructed with a=0.4 and b=0.6. These linear combination constants are optimized to obtain substantially constant ratio of the probe and reference temperature functions. Alternatively, two probe transitions can be chosen and a linear combination of their temperature functions be used to obtain a substantially constant ratio of probe and reference temperature functions.

The concentration of probe gas 12 is calculated once the constant (either based on a single reference transition or a linear combination of reference transitions) is entered into equation 5. In particular, the ratio of gases 12, 14 is measured. When the concentration of gas 14 is known then the concentration of gas 12 can be calculated from equation 5. In case there is a functional relationship between the concentration of gases 12, 14 the relationship is used to solve equation 5 for the concentration of gas 12. For example, the two gases are CO and $CO_2$ in car exhaust (for details see appendix A). The mathematical techniques for performing these operations are well-known to a person skilled in the art.

In another embodiment of the invention the spectroscopic technique employed is a broadband technique in which broadband sources are used in light beam generator 21. In this case the probe reaction and reference reaction can be total absorption or intensity reduction of the corresponding broadband radiation components in beam 30. In other words, many probe or reference spectroscopic transitions may exist within the corresponding spectral widths of the broadband sources chosen for probe and reference detection. The probe temperature function and reference temperature function are associated with the total intensity change of each broadband component chosen for detecting probe and reference species over the entire temperature range.

As in the previous embodiment, when one reference temperature function is insufficient to yield a ratio which is substantially constant over the temperature range, two broadband sources can be used to detect the reference species. Then, a linear combination of a first reference temperature function associated with the first broadband source and a second reference temperature function associated with the second broadband source can be used to obtain a substantially constant ratio of the probe and reference temperature functions. Alternatively, two broadband sources can be used to detect the probe species and obtain constant ratio of the probe and reference temperature functions.

Figure 4:
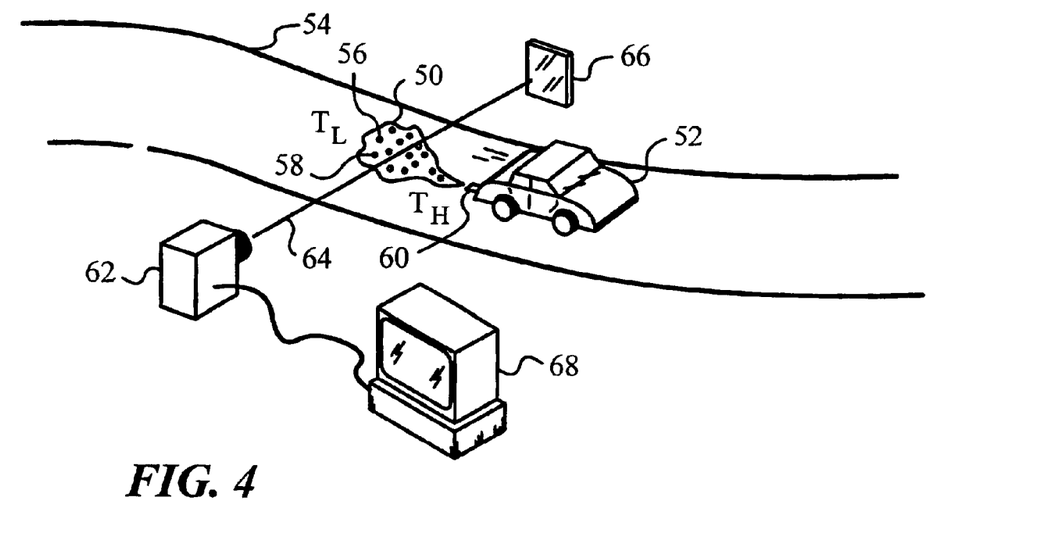
FIG. 4 is a three-dimensional view of an embodiment of the invention for monitoring vehicle emissions.

FIG. 4 illustrates an embodiment of the invention for measuring emissions in the form of a vehicle exhaust sample 50 produced by a vehicle 52 travelling on a road 54. In this embodiment the pollutant gas is CO and it is the probe gas 56 whose concentration in exhaust 50 is to be determined. Conveniently, $CO_2$ is selected as the reference gas 58. There is a functional relationship between CO and $CO_2$ since the total amount of C in car vehicle exhaust can be determined from the fuel composition and vehicle fuel economy. In other words, the functional relationship is $[CO]+[CO_2]=$ known value.

Vehicle exhaust 50 issues through a tail pipe 60 at a high temperature $T_H$. In this case $T_H$ can be estimated based on knowledge of internal combustion engines; specifically $T_H$ can be as high as 700° K. Upon exiting tail pipe 60 exhaust 50 cools to a low temperature $T_L$ equal to the ambient temperature of the surroundings, usually about 300° K. The actual temperature distribution and concentrations of gases making up exhaust sample 50 are highly non-uniform and unknown.

A remote sensing absorption spectrometer 62 is arranged along road 54. A light source (not shown) such as one or more lasers and/or broadband source or sources is integrated in spectrometer 62 to produce a test or probe beam 64 directed at exhaust sample 50. Optics 66, in this case a retroreflector, are positioned on the other side of road 54 for reflecting probe beam 64 back to spectrometer 62 for measurement. A computer 68 connected to spectrometer conveniently serves as a selection device for initially analyzing probe gas absorption transitions and reference gas absorption transitions to make the reference gas selection and transition selections as described above. Light sources are selected or adjusted to provide light containing wavelengths corresponding to the chosen absorption transitions.

Alternatively, if the measurements to be performed and environments where they will be performed are known and the gases as well as the relevant transitions are identified beforehand, the source wavelengths can be fixed. This can be the case where the reference gas is decided when designing and manufacturing the apparatus. In this situation the ratio of the temperature functions is also known and hence is not required in the sensor apparatus.

The measurement of probe gas concentration $[CO]_{meas}$ is performed in accordance with the method of invention.

In a particularly convenient embodiment, computer 68 also serves as a processing unit for using the measurement results obtained by spectrometer 62 and determining the concentration of probe gas 50, in this case $[CO]_{true}$, from the ratio of measured concentrations $[CO]_{meas}$ and $[CO_2]_{meas}$.

Alternatively, if a single-pass measurement is desired, optics 66 can be replaced by a detector unit to obtain measured concentrations $[CO]_{meas}$ and $[CO_2]_{meas}$. However, a retroreflector with the double-pass configuration is more convenient for field alignment.

The remaining object and advantages of the invention, as well as details of several specific embodiments are described in appendices A and B incorporated in this provisional patent application.

We claim:

1. A method for temperature-independent determination of a concentration of a probe gas in a sample, said method comprising:

a) selecting a temperature range;

b) selecting a first spectroscopic technique for the detection of said probe gas;

c) determining a probe temperature function of said probe gas over said temperature range for said first spectroscopic technique;

d) identifying in said sample a reference gas;

e) selecting a second spectroscopic technique for the detection of said reference gas;

f) determining a reference temperature function of said reference gas over said temperature range for said second spectroscopic technique such that a ratio of said probe temperature function to said reference temperature function is substantially constant over said temperature range;

g) measuring a probe reaction of said probe gas and a reference reaction of said reference gas with said first spectroscopic technique and said second spectroscopic technique; and h) deriving said concentration from said probe reaction and said reference reaction.

2. The method of claim 1, wherein said first spectroscopic technique and said second spectroscopic technique are the same.

3. The method of claim 1, wherein said first spectroscopic technique and said second spectroscopic technique comprise absorption spectroscopy employing a test beam. said probe reaction is a probe absorption of a wavelength component of said test beam chosen for the detection of said probe gas, and said reference reaction is a reference absorption of a wavelength component of said test beam chosen for the detection of said reference gas.

4. The method of claim 3, wherein said probe absorption and said reference absorption result from absorptive transitions.

5. The method of claim 4, wherein said absorptive transitions are selected from the group consisting of rovibrational transitions and rovibronic transitions of molecular gas species and from electronic transitions of atomic gas species.

6. The method of claim 3, wherein said probe absorption and said reference absorption result from absorptive transitions and a vector difference between said ratio and a constant value is used to select said absorptive transitions.

7. The method of claim 1, wherein said first spectroscopic technique and said second spectroscopic technique use at least one broadband light source.

8. The method of claim 7, wherein said reference temperature function is obtained from a linear combination of a first reference temperature function associated with a first broadband source and a second reference temperature function associated with a second broadband source.

9. The method of claim 7, wherein said probe temperature function is obtained from a linear combination of a first probe temperature function associated with a first broadband source and a second probe temperature function associated with a second broadband source.

10. The method of claim 1, wherein said first spectroscopic technique and said second spectroscopic technique use narrowband sources having spectral widths narrower than corresponding transition linewidths in said probe gas and said reference gas.

11. The method of claim 10, wherein said reference reaction comprises a first transition and a second transition, and said reference temperature function is obtained from a linear combination of a first reference temperature function of said first transition and a second reference temperature function of said second transition.

12. The method of claim 10, wherein said probe reaction is an attenuation resulting from a probe transition and said at least one narrowband source has a spectral width narrower than the linewidth of said probe transition.

13. The method of claim 1, further comprising:
a) deriving from said probe reaction and from said reference reaction a measured concentration ratio of said probe gas to said reference gas; and
b) using said measured concentration ratio in deriving said concentration.

14. The method of claim 1, wherein said temperature range is selected between a low temperature $T_L$ corresponding to a lowest temperature of said sample, and a high temperature $T_H$ corresponding to a highest temperature of said sample.

15. The method of claim 14, wherein said probe temperature function and said reference temperature function are indexed to a reference temperature $T_{ref}$ selected such that $T_L \leq T_{ref} \leq T_H$.

16. The method of claim 1, wherein said reference gas is a stable gas having a functional relationship with said probe gas.

17. The method of claim 14, wherein said functional relationship is used in deriving said concentration.

18. The method of claim 1, wherein said probe gas is CO.

19. The method of claim 18, wherein said reference gas is $CO_2$.

20. The method of claim 19, wherein said sample is a vehicle exhaust sample.

21. The method of claim 1, wherein said sample exhibits non-uniformities selected from temperature non-uniformities, pressure non-uniformities and gas composition non-uniformities.

22. The method of claim 1, wherein said ratio of said probe temperature function to said reference temperature function is substantially equal to one over said temperature range.

23. An apparatus for temperature-independent determination of a concentration of a probe gas in a sample over a temperature range by using a reference gas in said sample, said apparatus comprising:
a) a spectrometer for employing a first spectroscopic technique to measure a probe reaction of said probe gas and for employing a second spectroscopic technique to measure a reference reaction of said reference gas;
b) a processing unit connected to said spectrometer to receive said measure of said probe reaction of said probe gas and said measure of said reference reaction of said reference gas, and to determine from said measures a probe temperature function and a reference temperature function such that a ratio of said probe temperature function to said reference temperature function is substantially constant over said temperature range; and
c) a computing unit connected to said processing unit which derives said concentration of said probe gas from said temperature functions received from said processing unit.

24. The apparatus of claim 23, further comprising a unit for calculating said ratio.

25. The apparatus of claim 23, wherein said spectrometer comprises at least one broadband light source.

26. The apparatus of claim 23, wherein said spectrometer comprises at least one narrowband source.

27. The apparatus of claim 26, wherein said narrowband source comprises a single-longitudinal-mode laser.

28. The apparatus of claim 23, further comprising optics for directing a test beam of said spectrometer.

* * * * *